United States Patent
Lu et al.

(10) Patent No.: US 9,132,111 B2
(45) Date of Patent: Sep. 15, 2015

(54) TOPICAL ANTIMICROBIAL COMPOSITIONS

(76) Inventors: Kewang Lu, Dover, DE (US); Hoshun Luk, New York, NY (US); Lei Zhang, Kunming (CN)

( * ) Notice: Subject to any disclaimer, the term of this patent is extended or adjusted under 35 U.S.C. 154(b) by 1113 days.

(21) Appl. No.: 13/067,167

(22) Filed: May 13, 2011

(65) Prior Publication Data

US 2012/0289575 A1 Nov. 15, 2012

(51) Int. Cl.
- *A01N 43/38* (2006.01)
- *A61K 31/40* (2006.01)
- *A01N 43/36* (2006.01)
- *A61K 31/198* (2006.01)
- *A61K 31/4015* (2006.01)

(52) U.S. Cl.
CPC ............ *A61K 31/198* (2013.01); *A61K 31/4015* (2013.01)

(58) Field of Classification Search
USPC ........................................................ 514/413
See application file for complete search history.

(56) References Cited

U.S. PATENT DOCUMENTS

| 4,016,287 A * | 4/1977 | Eberhardt et al. ............ 514/617 |
| 2012/0107415 A1 * | 5/2012 | Lisowsky et al. ............ 424/615 |

FOREIGN PATENT DOCUMENTS

WO      WO 9721348 A1 * 6/1997

* cited by examiner

*Primary Examiner* — Layla Soroush
(74) *Attorney, Agent, or Firm* — Mendelson IP; Elliot C Mendelson

(57) ABSTRACT

Disclosed are topical antimicrobial compositions. The compositions are useful for disinfecting and treating microbial infections of the skin or mucosa of humans and animals. The antimicrobial compositions include a salt of amino acid anion and quaternary ammonium cation, comprising the general formula:

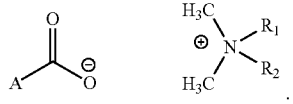

5 Claims, No Drawings

TOPICAL ANTIMICROBIAL COMPOSITIONS

FIELD OF THE INVENTION

The present invention relates to topical anti-microbial compositions and methods of disinfecting and treating microbial infections of the skin or mucosa. In particular, the present invention relates to methods and compositions utilizing an amino acid carboxylic salts comprised of amino acid anions and quaternary ammonium cations.

BACKGROUND OF THE INVENTION

Disinfectants are grouped in seven categories. Each of them has some short comings: Alcohol-based agents have wide germicidal activity but poses a fire hazard, provide limited activity in the presence of organic matter, not effective against bacterial and fungal spores. Alcohol-based agents are also in general too expensive. Halogens (Iodine or hypochlorite) are corrosive, have limited activity when in the presence of organic matter, not effective as sporocidal agent and they may stain surfaces. Phenolics (single or multiple) are not sporocidal and are potentially mutagenic. Tar distillates (cresol and cresylic acid) are not sporocidal, but are corrosive and toxic at high concentrations and emit noxious gases. Aldehydes (Glutaraldehyde) are toxic and are mutagens. Oxidizing agents (hydrogen peroxide, potassium permanganate) are not sporocidal, ineffective in the presence of organic matter;

The biocidal activities of quaternary ammonium compositions have been reported. It was noted that didecyldimethyl ammonium compounds, and particularly didecyldimethylammonium chloride, are potential biocides. Preston, J.A.O.C.S. 60:567 (1983) concurs and suggests that maximum fungi-toxicity is exhibited with dialkyldimethyl compounds having $C_{10}$-$C_{12}$ alkyl groups.

Ruseggan, in U.K. Patent Publication No. 650,304, discloses a detergent which includes a tetra alkyl quaternary ammonium halide or hydroxide in which two alkyl groups contain from 6 to 9 carbon atoms in each hydrocarbon group and the other two alkyl groups contain 3 to 9 carbon atoms each together with a weak alkali. Such compositions may also include an alkali substrate (U.K. Patent Publication No. 669, 506). Quaternary ammonium compounds have advantages over alcohol-based products. First, although quaternary ammonium compounds are broadly effective antimicrobials, these compounds demonstrate relatively low toxicity to animals. Second, quaternary ammonium compounds are essentially odorless, making them easy to formulate in personal care products. Finally, quaternary ammonium compounds do not degrade or corrode materials, such as steel, plastics, and rubber.

U.S. Pat. No. 6,297,285 presented a method for disinfecting a substrate with a biocidal effective amount of a composition of one quaternary ammonium carbonate, bicarbonate, or any combination thereof, a solvent and a surfactant.

Quaternary ammonium compounds, such as benzalkonium chloride, possess antimicrobial activity against a wide range of microbial pathogens, including bacteria, fungi, and viruses. U.S. Pat. No. 7,754,770 uses benzalkonium chloride in antimicrobial composition in a format for no-rinse application to the skin. The formulation tested showed positive eye irritation in accordance with OPPTS 870, 2400 Guidelines. The tested compound is classified as Toxicity category III, indicating corneal involvement or irritation (U.S. Pat. No. 7,754,770, column, line 55). Although benzalkonium chloride is widely used, but it may cause reproductive defects and may act as a mutagen.

When degraded some alkyl quaternary ammonium chloride tends to form organic chloride which is toxic and mutagenic.

With increased concerns over pathogens in the household and environment, the need for safe disinfectants and sanitizers has increased. Especially with the epidemic spread of SARS, swine flu (H1N1 flu), aviation flu and hand-foot-mouth diseases, there is a continuing and urgent need for safe and strong disinfectant which is not toxic nor cause skin or ocular irritation.

DETAILED DESCRIPTION OF THE INVENTION

The present invention relates to topical compositions for disinfecting and treating microbial infections of the skin or mucosa. The topical compositions relates to a new type of biocidal compounds and the preparation thereof. The new type bactericidal compounds are amino acid carboxylic salts comprised of amino acid anions and non-halogenated quaternary ammonium cations, comprising the general formula:

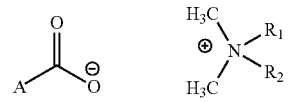

Wherein A-COO⁻ is protected amino acid, wherein A is different feasible amino acid residue derivatives.
Wherein R1 is cyclic or acyclic aliphatic substituent moieties or aromatic moieties which may themselves be substituted by aliphatic, cyclic, acyclic, or alkyloxy groups,
Wherein R2 is aromatic moieties which may themselves be substituted by aliphatic, alicyclic, alkyloxy groups.
R1 or R2 could be the same or different.
R1 or R2 could be H
Wherein the quaternary ammonium group could be other cationic groups, including but not limited to phosphonium or sulfonium, or any other positive nonmetallic nuclei that are feasible to generate a positive charge.

The amino acid carboxylic salts in the present invention are comprised of amino acid anions and quaternary ammonium cation.

A preferred quaternary ammonium amino acid carboxylate salt is one in which R1 is a $C_1$-$C_{30}$ alkyl or aryl-substituted alkyl group and R2 is a $C_8$-$C_{20}$ alkyl group. Preferably, R1 and R2 are the same C8-C20 alkyl group.

Aromatic moieties, which may themselves be substituted by aliphatic, alicyclic, alkyloxy groups, useful as substituents for the quaternary cationic salts of the present invention are benzyl, tolyl, xylyl, naphthyl, pyridyl, benzal, quinolyl and the like. More specifically, some aliphatic quaternary ammonium salts which are useful in the present invention are: tetramethyl ammonium halide, trimethylethyl ammonium halide, dimethyldiethyl ammonium halide, methyltriethyl ammonium halide, tetraethyl ammonium halide, cetyldimethylethyl ammonium halide, trimethyl n-propyl ammonium halide, dimethyl di n-propyl ammonium halide, methyl tri n-propyl ammonium halide, tetra n-propyl ammonium halide, methylethyl n-propyin-butyl ammonium halide, ethyl n-propyinpentyl ammonium halide, trimethylallyl ammonium halide, dimethyldiallyl ammonium halide, methyltriallyl ammonium halide, tetraallyl ammonium halide, N,N,N,N',N',N'-hexaethyl-1,2-ethylene diammonium halide, N,N, N,N',N',N'-hexaethyl-1,4-butylene diammonium halide, N,N,N'-dibenzyl-N,N,N',N', tetramethyl-1,2-ethylene diammonium halide, N,N'-di(4-chlorobenzyl)-N,N,N',N'-tetramethyl-1,2-ethylenediammoniumhalide, N,N,N'-tetraethyl-N,n''-di-octadecyl-4,2-ethylene diammonium halide, N,N,N',N'-tetraethyl-N,N'-dihexadecyl-1,4-butylene diammonium halide, octadecyltrimethyl ammonium halide, dioctadecyldimethyl ammonium halide, trioctadecylmethyl ammonium halide tetraoctadecyl ammonium halide, hexadecyltriethyl ammonium halide, hexadecyldimethylethyl ammonium halide, hexadecyl-diethylmethyl ammonium halide, didecyldioctyl ammonium halide, didecyldihexyl ammonium halide, and hexyloctyldecyldodecyl ammonium halide.

Some representative useful quaternary ammonium salts containing an aromatic moiety include: benzyldodecyldimethyl ammonium halide, o-tolyldodecyldimethyl ammonium halide, m-tolyldodecyldimethyl ammonium halide, p-tolyldodecyldimethyl ammonium halide, 2,3-xylyl-dodecyldimethyl ammonium halide, 2,4-xylydodecyldimethyl ammonium halide, 2,5-xylyl-dodecyldimethyl ammonium halide, 3,4-xylyldodecyldimethyl ammonium halide, 3,5-xylyl-dodecyldimethyl ammoniuim halide, 2-chlorobenzyldodecyldimethyl ammonium halide, 3-chloro-benzyldodecyldimethyl ammonium halide, 4-chlorobenzyldodecyldimethyl ammonium halide, 2,3-dichlorobenzyldodecyldimethyl ammonium halide, 2,4-dichlorobenzyldodecyldimethyl ammonium halide, 2,5-dichlorobenzyldodecyldimethyl ammonium halide, 2,6-dichlorobenzyl-dodecyldimethyl ammonium halide, 3,4-dichlorobenzyldodecyldimethyl ammonium halide, 3,5-dichlorobenzyldodecyldimethyl ammonium halide, 2-nitrobenzyldodecyldimethyl ammonium halide, 3-nitrobenzyldodecyldimethyl ammonium halide, 4-nitrobenzyldodecyldimethyl ammonium halide, 2,4-dinitrobenzyldodecyldimethyl ammonium halide, 3,5-dinitrobenzyldodecyldimethyl ammonium halide, 2-sulfobenzyldodecyldimethyl ammonium halide, 3-sulfobenzyldodecyldimethyl ammonium halide, 4-sulfobenzyldodecyldimethyl ammonium halide, 2-carboxybenzyldodecyldimethyl ammonium halide, 3-carboxybenzyl-dodecyldimethyl ammonium halide, 4-carboxybenzyldodecyldimethylammonium-halide, benzyl hexyl dimethyl ammonium halide, benzyl octyl dimethyl ammonium halide, benzyl decyl-dimethyl ammonium halide, benzyl dodecyl dimethyl ammonium halide, benzyl tetradecyl dimethyl ammonium halide, benzylhexa decyl dimethyl ammonium halide, benzyl octa decyl dimethyl ammonium halide.

Some of the aliphatic or alicyclic substituents for the quaternary ions are alkyl groups containing one to 30 carbon atoms both linear and branched, alkoxy groups also containing one to 30 carbon atoms both linear and branched, alicyclic groups such as cyclohexyl and its alkylated or alkyloxylated derivatives, and halogenated alkyl, aromatic moieties include: n-hexylpyridinium halide, n-octylpyridinium halide, n-decylpyridinium halide, n-dodecylpyridinium halide, n-tetradecylpyridinium halide, n-hexadecylpyridinium halide, n-hexyllutidinium halide, n-octyllutidinium halide, n-decyllutidinium halide, n-dodecyllutidinium halide, n-tetradecyllutidinium halide, n-hexadecyllutidinium halide, n-hexylpicolinium halide, n-octylpicolinium halide, n-decylpicolinium halide, n-dodecylpicolinium halide, n-tetradecylpicolinium halide, n-hexadecylpicolinium halide, n-hexylquinolinium halide, n-octylquinolinium halide, n-decylquinolinium halide, n-dodecylquinolinium halide, n-tetradecylquinolinium halide, n-hexadecylquinolinium halide, n-hexylisoquinolinium halide, n-octylisoquinolinium halide, n-decylisoquinolinium halide, n-dodecylisoquinolinium halide, n-tetradecylisoquinolinium halide, n-hexadecylisoquinolinium halide, n-hexylquinazolinium halide, n-octylquinazolinium halide, n-decylquinazolinium halide, n-dodecylquinazolinium halide, n-tetradecylquinazolinium halide, n-hexadecylquinazolinium halide, n-hexylquinoxalinium halide, n-octylquinoxalinium halide, n-decylquinoxalinium halide, n-dodecylquinoxalinium halide, n-tetradecylquinoxalinium halide, n-hexadecylquinoxalinium halide, n-hexylpyridopyridinium halide, n-octylpyridopyridinium halide, n-decylpyridopyridinium halide, n-dodecylpyridopyridinium halide, n-tetradecylpyridopyridininum halide, and n-hexadecylpyridopyridinium halide.

Amino acids could be used include:

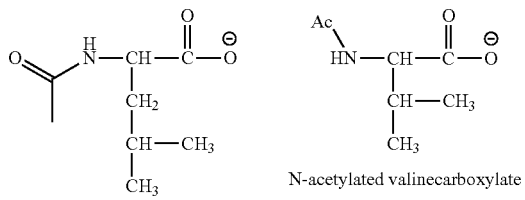

N-acetylated leucine carboxylate

N-acetylated valinecarboxylate

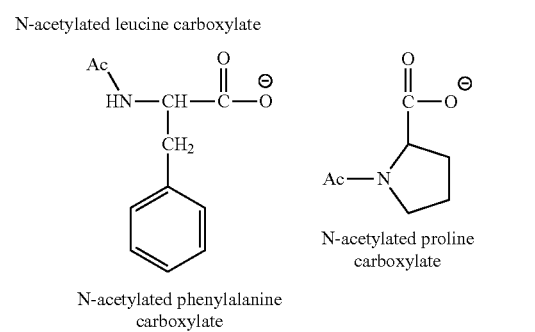

N-acetylated phenylalanine carboxylate

N-acetylated proline carboxylate

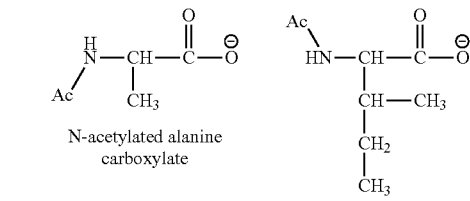

N-acetylated alanine carboxylate

N-acetylated isoleucine carboxylate

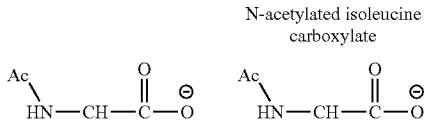

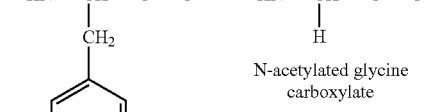

N-acetylated glycine carboxylate

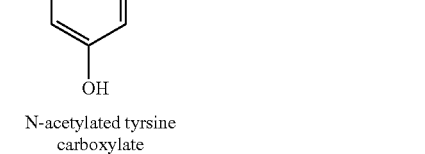

N-acetylated tyrsine carboxylate

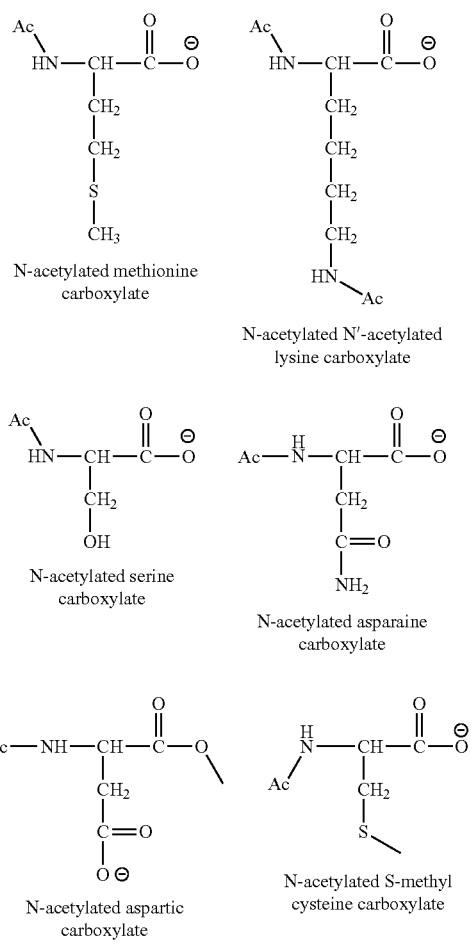

In the above structures, Ac stands for acetyl group, $CH_3C=O-$

Acetyl group is bound to the amino group of amino acid to remove the positive charge. The generic amino acid in water is of the following general structure:

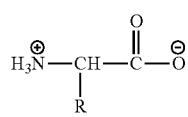

In order to make it an anion for use as counter ion for the quaternary ammonium amino salt, the positive charge need to be removed by, most often, acetylation;

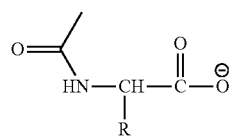

Some of the amino acid residues have side chains that are both charged and chemically reactive, such as cystine, lysine and aspartic acid. The chemical reactivity will be removed for the present invention. In the case of cystine, a methyl group is tethered to the thiol (—SH) group to generate —$SCH_3$. Thiol (—SH) group is reactive and can cause several covalent chemical reactions, —$SCH_3$ is more stable and inert.

A series of ammonium salts with different organic anions can be prepared by the following general procedures. First, an organic acid is neutralized by one equivalent of metal hydroxide (such as NaOH or KOH) in volatile organic solvents, such as methanol, ethanol, or in water at low temperature maintained by an ice bath or an acetone thy ice slurry. Second, the volatile organic solvent or water is removed by vacuum to obtain the corresponding salt of metal organic anion in solid form. Third, the metal cation organic anion salt is dissolved in water and mixed with one equivalent of the organic ammonium chloride. Forth, organic solvent is added to the aqueous solution to form two layers, of which the organic components (organic anions and organic ammonium cations) is partitioned in the organic phase, and the byproduct metal cation and inorganic anion remain in the aqueous solution. Fifth, the organic solvent is separated from the aqueous layer and is evaporated by a Rota vapor. Sixth, the aqueous portion is mixed with pure organic solvent to extract more organic salt from the aqueous solution. This extraction is repeated 3 times. Seventh, the organic extracts are combined, and the organic solvent is removed by vacuum to obtain the desired product.

EXAMPLES

Example 1

Preparation of N,N-di-n-decyl-N,N-dimethyl-ammonium 5-oxopyrrolidine-2-carboxylate (DAPC)

1. Dissolve 0.03 mol NaOH in deionized water, make the total weight 30 g and cool it to room temperature.

2. Dissolve D-Pyroglutamic acid (2-Pyrrolidone-5-carboxylic acid) 0.03 mol in the above solution containing 30 g NaOH, stirring for 10 min. the reaction product is an aqueous solution of Sodium D-Pyroglutamic acid (solution A).

3. Dissolve 0.025 mol N,N-di-n-decyl, N-didimethylammonium chloride in 160 g deionized water, (solution B).

4. mix solution A and solution B to obtain solution C.

5. Transfer solution C to an extraction flask, add 400 ml organic solvent and 10 gram sodium chloride to the flask, mix well and let it stand for 30 min to separate in two layers.

6. The organic solvent is separated from the aqueous layer and is evaporated by a Rota vapor to obtain product DAPC.

7. The aqueous portion is mixed with pure organic solvent to extract more organic salt from the aqueous solution. This extraction is repeated 3 times. The organic extracts are combined, and the organic solvent is removed by vacuum. 8.7 g DAPC was obtained.

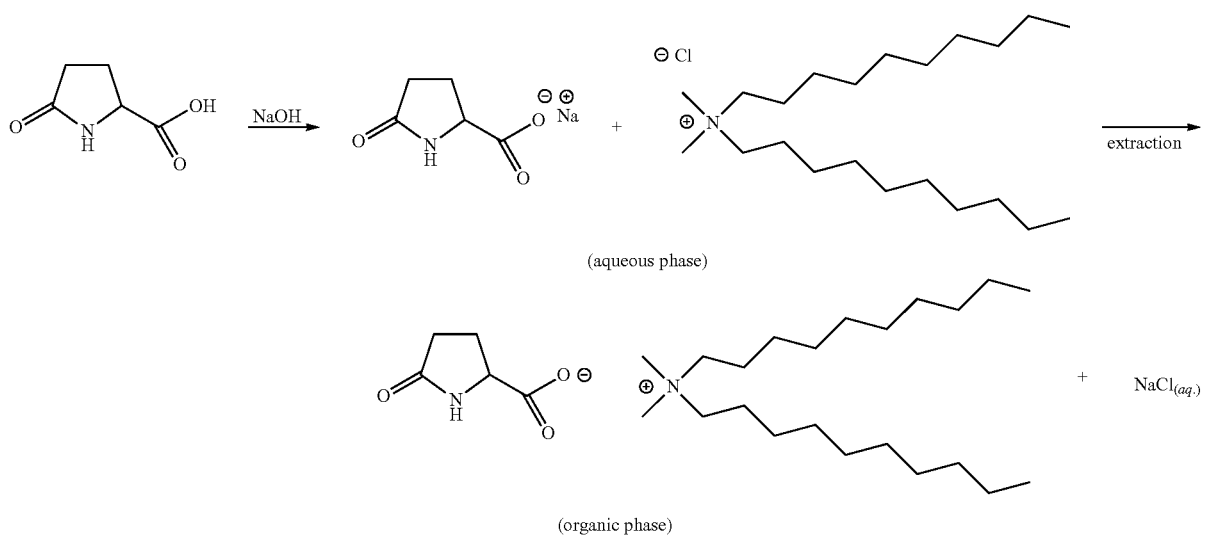

Example 2

Preparation of N,N-di-n-decyl-N,N-dimethyl-ammonium N-acetylatedal alanine carboxylate (DAAC)

1. Dissolve 0.03 mol NaOH in deionized water, make the total weight 30 g and cool it to room temperature.

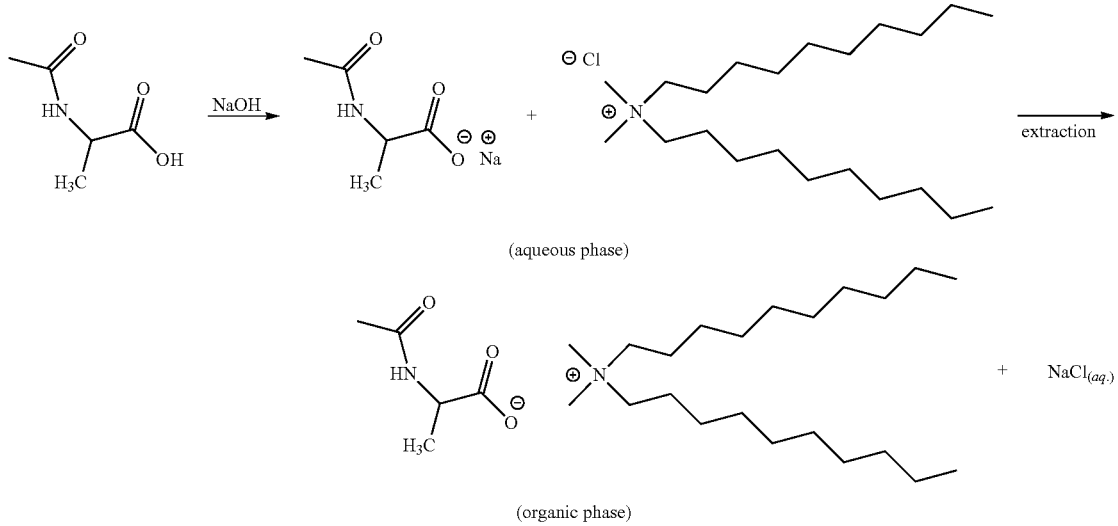

2. Dissolve acetylated alanine acid (2-Pyrrolidone-5-carboxylic acid) 0.03 mol in the above solution containing 30 g NaOH, stirring for 10 min. The reaction product is an aqueous solution of Sodium acetylated alanine acid (solution A).
3. Dissolve 0.025 mol N,N-di-n-decyl, N-didimethylammonium chloride in 160 g deionized water, (solution B).
4. mix solution A and solution B to obtain solution C.
5. Transfer solution C to an extraction flask, add 400 ml organic solvent and 10 gram sodium chloride to the flask, mix well and let it stand for 30 min to separate in two layers.
6. The organic solvent is separated from the aqueous layer and is evaporated by a Rota vapor to obtain product DAPC.
7. The aqueous portion is mixed with pure organic solvent to extract more organic salt from the aqueous solution. This extraction is repeated 3 times. The organic extracts are combined, and the organic solvent is removed by vacuum. 9.0 g DAAC was obtained.

Example 3

Other examples can be prepared accordingly, including:

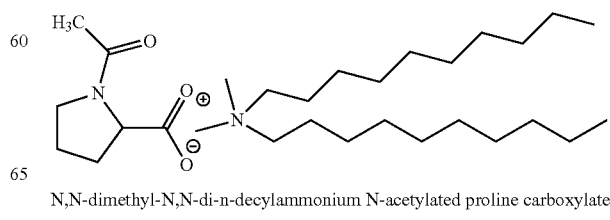

N,N-dimethyl-N,N-di-n-decylammonium N-acetylated proline carboxylate

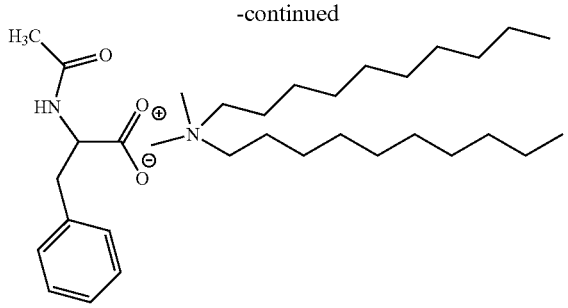

N,N-dimethyl-N,N-di-n-decylammonium N-acetylated phenylalanine carboxylate

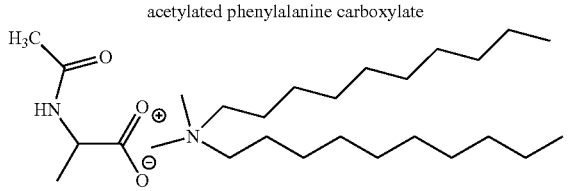

N,N-dimethyl-N,N-di-n-decylammonium N-acetylated alanine carboxylate

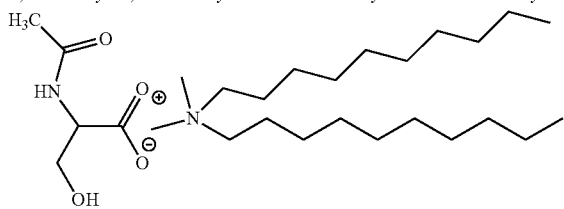

N,N-dimethyl-N,N-di-n-decylammonium N-acetylated serine carboxylate

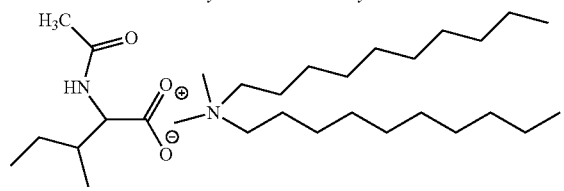

N,N-dimethyl-N,N-di-n-decylammonium N-acetylated isoleucine carboxylate

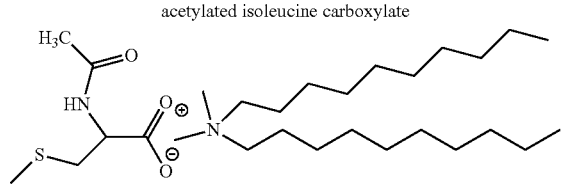

N,N-dimethyl-N,N-di-n-decylammonium N-acetylated cystine carboxylate

Example 4

The following formulation examples are merely exemplary and are not intended to limit the scope of the invention.

TABLE 1

Formulation of Antimicrobial Composition

| | Formulation | | | | | |
|---|---|---|---|---|---|---|
| | 1 | 2 | 3 | 4 | 5 | 6 |
| DAPC | 0.10 | 1.20 | 0.003 | 0.006 | 0.0016 | 0.0008 |
| DAAC | | 1.20 | | | | |
| NaCl | 0.10 | 0.10 | 0.003 | 0.006 | 0.0016 | 0.0008 |
| DH2O | 99.80 | 97.50 | 99.994 | 99.988 | 99.997 | 99.998 |

DAPC: N,N-di-n-decyl-N, N-dimethyl-ammonium 5-oxopyrrolidine-2-carboxylate

DAAC: N,N-di-n-decyl-N, N-dimethyl-ammonium N-acetylatedal alanine carboxylate

Example 5

Acute Oral Toxicity Test

The purpose of this experiment is to assess the acute toxicity of the antimicrobial composition administered orally in a single dose with a 14-day post-administration observation procedure.

1. Materials

Testing animal: 20 SPF grade Kunming white mise (10 male and 10 female), provided by the animal center of Kunming Medical University Test material: Formulation 1

Environment: Temp. 20-23° C.; humidity 50-70%.

2. Testing Methods and Standards:

1) Standard: <<Technical Standard for Disinfection>> (2002 Edition), Acute Oral Toxicity tests 2) Method: the largest limitation method was used. The dose was set up at 5000 mg/kg.bw. 20 animal was used (10 male, 10 female); body weight 18.0-22.0 gm, the animal was fasted for 15 hours before feed the test sample, animals were fed 0.2 ml/10 g.bw at one time; observe testing animals for 14 days and record the toxic appearance and the mortality.

3. Results

There was no abnormality of the animals observed during the experimental period, the increases of body weight are normal, no mortality. The autopsies did not disclose any pathological change in all of the animals.

TABLE 2

Results of Mouse Acute Oral Toxicity Tests

| Animal gender | Dosage (mg/kg · bw) | Animal tested | Mortality | Death rate (%) |
|---|---|---|---|---|
| female | 5000 | 10 | 0 | 0 |
| Male | 5000 | 10 | 0 | 0 |

4. Conclusion

Under the testing conditions, the $LD_{50}$ of the test sample was larger than 5000 mg/kg.bw. According to grading standards of the evaluation, the tested material is not toxic.

Example 6

Acute Eye Irritation Tests

1. Materials and Methods:
1) Testing animal: Three New Zealand rabbits. Provided by "the Animal Center of Kunming Medical University"
2) Test material: Formulation 1
3) Environment: Temp. 18-22° C.; humidity 48-50%.
4) Method:
a. Standard: Eye irritation tests <<Technical Standard for Disinfection>> (2002 Edition)
b. Drop 0.1 ml sample into the conjunctiva cyst of one eye of the animal
c. Close the eye lids for 4 seconds
d. Use the other eye as control
e. Rinses the eye with saline after 30 seconds.
f. Exam the eye after 1 h., 24 h., 48 h., 72 h., 7 day, 14 day and 21 days.
g. If there were no irritation reactions after 72 h. or the reactions recovered at $7^{th}$ day or $14^{th}$ day, terminate the tests.
h. Calculates the average scores of cornea damage, iris damage, conjunctiva congestions and edema at 24 h., 48 h., 72 h.
i. Determine the irritation degree of the sample using the criteria of the standard.
2. Results There was no abnormality of the animal eyes observed during the experimental period. The scores of eye irritations are shown in table 3.

3. Conclusion

Under the testing conditions, according to the grading criteria of acute eye irritation tests, the tested material had no irritation to rabbit eyes.

Example 7

Skin Irritation Tests

1. Materials
1) Testing animal: Three Regular Japanese Rabbits. Provided by "the Animal Center of Kunming Medical University"
2) Test material: Formulation 1
3) Environment: Temp. 20-22° C.; humidity 60-63%.
2. Testing methods and standards Standard: <<Technical Standard for Disinfection>> (2002 Edition)

Methods: 24 hours before testing remove the rabbit back hair (both sides of spine) about 3 cm×3 cm. Smear 1.0 ml sample (Formulation 1) on the hair removed skin (2.5 cm×2.5 cm), cover with two layers of gauze, fixed with adhesive tape. The other side used saline as blank control. Remove the gauze and the test sample with lukewarm water after 4 hours. Examine the local skin reaction at 1 h., 24 h. and 48 h. and record the scores.

3. Results

There was no abnormality of the animal skin observed during the experimental period. The Reaction scores of test sample to rabbit skin are shown in table 4.

TABLE 3

Acute Eye Irritation Tests of Antimicrobial Composition

| | | Scores of eye irritations | | | | | | | | |
|---|---|---|---|---|---|---|---|---|---|---|
| | | 1 h. | | 24 h. | | 48 h. | | 72 h. | | Average score | |
| Animal Number | Examined area | Sample | Control | Sample | Control | Sample | Control | Sample | Control | Sample | Control |
| 1 | cornea damage | 0 | 0 | 0 | 0 | 0 | 0 | 0 | 0 | 0 | 0 |
| | iris damage | 0 | 0 | 0 | 0 | 0 | 0 | 0 | 0 | 0 | 0 |
| | conjunctiva erythema | 0 | 0 | 0 | 0 | 0 | 0 | 0 | 0 | 0 | 0 |
| | conjunctiva edema | 0 | 0 | 0 | 0 | 0 | 0 | 0 | 0 | 0 | 0 |
| 2 | cornea damage | 0 | 0 | 0 | 0 | 0 | 0 | 0 | 0 | 0 | 0 |
| | iris damage | 0 | 0 | 0 | 0 | 0 | 0 | 0 | 0 | 0 | 0 |
| | conjunctiva erythema | 0 | 0 | 0 | 0 | 0 | 0 | 0 | 0 | 0 | 0 |
| | conjunctiva edema | 0 | 0 | 0 | 0 | 0 | 0 | 0 | 0 | 0 | 0 |
| 3 | cornea damage | 0 | 0 | 0 | 0 | 0 | 0 | 0 | 0 | 0 | 0 |
| | iris damage | 0 | 0 | 0 | 0 | 0 | 0 | 0 | 0 | 0 | 0 |
| | conjunctiva erythema | 0 | 0 | 0 | 0 | 0 | 0 | 0 | 0 | 0 | 0 |
| | conjunctiva edema | 0 | 0 | 0 | 0 | 0 | 0 | 0 | 0 | 0 | 0 |

TABLE 4

Results of Rabbit Skin Irritation Test

| | | | 1 h | | | | | | 24 h | | | | | |
| --- | --- | --- | --- | --- | --- | --- | --- | --- | --- | --- | --- | --- | --- | --- |
| | | Body | sample | | | control | | | sample | | | control | | |
| Animal Number | Gender | Weight (kg) | Erythema | Edema | Total scores | Erythema | Edema | Total scores | Erythema | Edema | Total scores | Erythema | Edema | Total scores |
| 1 | ♀ | 2.6 | 0 | 0 | 0 | 0 | 0 | 0 | 0 | 0 | 0 | 0 | 0 | 0 |
| 2 | ♀ | 2.4 | 0 | 0 | 0 | 0 | 0 | 0 | 0 | 0 | 0 | 0 | 0 | 0 |
| 3 | ♂ | 2.6 | 0 | 0 | 0 | 0 | 0 | 0 | 0 | 0 | 0 | 0 | 0 | 0 |
| Ave. score | | | | 0 | | | 0 | | | 0 | | | 0 | |

| | | | 48 h | | | | | |
| --- | --- | --- | --- | --- | --- | --- | --- | --- |
| | | Body | sample | | | control | | |
| Animal Number | Gender | Weight (kg) | Erythema | Edema | Total scores | Erythema | Edema | Total scores |
| 1 | ♀ | 2.6 | 0 | 0 | 0 | 0 | 0 | 0 |
| 2 | ♀ | 2.4 | 0 | 0 | 0 | 0 | 0 | 0 |
| 3 | ♂ | 2.6 | 0 | 0 | 0 | 0 | 0 | 0 |
| Ave. score | | | | 0 | | | 0 | |

4. Conclusion

Under the testing conditions, according to the irritation grading criterion, testing material had no irritation to the skin of the testing animals for the one time skin irritation tests.

Example 8

Skin Hypersensitivity Tests

1. Materials
1) Testing animals: 48 regular Guinea pigs (24 females, 24 males, provided by "the Animal Center of Kunming Medical University"
2) Test material: Formulation 1
3) Grouping: the animals were randomly divided into three groups, testing group; negative control group and positive control group. Each group had 16 animals.
5) Positive group used 2.4 dimethoxy-4-nitrochlorobenzene dissolved in dimethyl sulphoxide.
6) Environment: Temp. 20-22° C.; humidity 60-63%.
2. Testing Methods and Standards
  1) Standard: <<Technical Standard for Disinfection>> (2002 Edition)
Skin Hypersensitivity Tests, Page: 134
2) 24 hours before testing shave the back of animal to expose 3 cm×3 cm skin.
Inducing: smear 0.5 ml sample on the left side of the exposed skin, covered with two layers of gauze, and fixed with adhesive tapes for 6 hours Repeat step 2 at $7^{th}$ and $14^{th}$ day.

3) Positive control: Use 0.5 ml of 0.2% 2.4 dimethoxy-4-nitrochlorobenzene treat the animal in the same way.

4) Negative control: use 0.5 ml saline treated the same way.

5) Agitation: two weeks after the last inducing treatment

6) Smear 0.5 gm sample at the right side of the exposed skin, keep six hours.

7) Remove the cover after 24 h. and examine the skin reaction and at 48 h.

8) Determine the reaction degree according to the standard.

3. Results

TABLE 5

Results of Guinea Pigs Skin Hypersensitivity Tests

| Group | Sample Size | Inducing Conc. | Agitating Conc. | Time | Deg. of Erythema | | | | | Deg. of Edema | | | | Reaction Rate |
| --- | --- | --- | --- | --- | --- | --- | --- | --- | --- | --- | --- | --- | --- | --- |
| | | | | | 0 | 1 | 2 | 3 | 4 | 0 | 1 | 2 | 3 | |
| Testing Group | 16 | 0.5 ml | 0.5 ml | 24 h. | 16/16 | | | | | 16/16 | | | | 0 |
| | | | | 48 h. | 16/16 | | | | | 16/16 | | | | 0 |
| Negative Control | 16 | 0.5 ml | 0.5 ml | 24 h. | 16/16 | | | | | 16/16 | | | | 0 |
| | | | | 48 h. | 16/16 | | | | | 16/16 | | | | 0 |
| Positive Control | 16 | 0.5 ml | 0.5 ml | 24 h. | | | 9/16 | 7/16 | | | 8/16 | 8/16 | | 100 |
| | | | | 48 h. | | 4/16 | 12/16 | | | | | 16/16 | | 100 |

4. Conclusion

Under the testing conditions, there was no hypersensitive reaction observed on the testing animals for the hypersensitive reaction of the tested material.

Efficacy of Antimicrobial Composition

Example 9

Effects of the Antimicrobial Composition Against *Candida albicans*

1. Materials
1) Testing strain: *Candida albicans* ATCC 10231, the 5-6 generations; provide by the "Reserve Center of Chinese Microbial Reservation Committee".

2) Testing sample: Formulation 1. The testing sample was diluted for 2, 4, 8, 16, 32, 64, 128 and 264 times using standard hard water, then reacted with ATCC 10231 for 1 min, 5 min, 10 min.
2. Testing Methods and Standards:
<<Technical Standard for Disinfection>> (2002 Edition) GB15979-2002 <<Technical standard for testing disinfection product>> "Procedures for testing bactericide effect"
3. Results
The bactericidal effect of antimicrobial composition against *Candida albicans* ATCC10231 at 20±1° C. temperature is shown in table 6.

TABLE 6

The MIC of Antimicrobial Composition to *Candida albicans*

| time (min) | Dilution levels with related (CFU/mL) and kill rate (%) | | | | | | | Positive control |
|---|---|---|---|---|---|---|---|---|
| | 4 folds | 8 folds | 16 folds | 32 folds | 64 folds | 128 folds | 256 folds | |
| 1 | 100 | 100 | 100 | 100 | 100 | 98.82 | — | 7.0 × $10^4$ |
| 5 | 100 | 100 | 100 | 100 | 100 | 100 | 93.45 | |
| 10 | 100 | 100 | 100 | 100 | 100 | 100 | 99.71 | |

4. Conclusion
The testing sample was reacted with *Candida albicans* ATCC10231 for 1 min, 5 min, 10 min. The minimum inhibiting concentrations of the DDAPC are 0.0016% (formulation 5), 0.0008% (formulation 6), 0.0004% (formulation 7) respectively.

Example 10

Effects of the Antimicrobial Composition Against *Staphylococcus aureus*

1. Materials
1) Testing strain: *Staphylococcus aureus* ATCC6538, 5-6th generations, provided by the reserve center of China microbial reservation committee.
2) Testing sample: Formulation 1. The testing sample was diluted for 2, 4, 8, 16, 32, 64, 128 and 264 folds using standard hard water, then reacted with ATCC6538 for 1 min, 5 min, 10 min.
2. Testing Methods and Standards:
<<Technical Standard for Disinfection>> (2002 Edition) GB15979-2002 <<Technical standard for testing disinfection product>> "Procedures for testing bactericide effect"
3. Results
The Bactericide effect of Antimicrobial Composition against *Staphylococcus aureus* is shown in table 7.

TABLE 7

The MIC of Antimicrobial Composition to *Staphylococcus aureus*

| time (min) | Dilution levels with related (CFU/mL) and kill rate (%) | | | | | | | Positive control |
|---|---|---|---|---|---|---|---|---|
| | 4 times | 8 times | 16 times | 32 times | 64 times | 128 times | 256 times | |
| 1 | 100 | 100 | 100 | 100 | 100 | 98.82 | — | 7.0 × $10^4$ |
| 5 | 100 | 100 | 100 | 100 | 100 | 100 | 93.45 | |
| 10 | 100 | 100 | 100 | 100 | 100 | 100 | 99.71 | |

4. Conclusion
The testing sample was reacted with *Staphylococcus aureus* ATCC6538 for 1 min, 5 min 10 min. The minimum inhibiting concentrations of the DDAPC are 0.0016% (formulation 5), 0.0004% (formulation 7), 0.0004% (formulation 7) respectively.

Example 11

Effects of the Antimicrobial Composition Against *Eschetichia coli*

1. Materials
1) Testing strain: *Eschetichia coli* 8099, the 5-6 generations were used; provide by the "Reserve Center of Chinese Microbial Reservation Committee".
2) Testing sample: Formulation 1. The testing sample was diluted for 2, 4, 8, 16, 32, 64, 128 and 256 folds using standard hard water, then reacted with *Eschetichia coli* 8099 for 1 min, 5 min, 10 min.
2. Testing Methods and Standards:
<<Technical Standard for Disinfection>> (2002 Edition) GB15979-2002 <<Technical standard for testing disinfection product>> "Procedures for testing bactericide effect"
3. Results
The bactericide effect of testing sample against *Eschetichia coli* 8099 at 20±1° C. temperature is shown in Table 8.

TABLE 8

The MIC of Antimicrobial Composition to *Eschetichia coli*

| time (min) | Dilution levels with related (CFU/mL) and kill rate (%) | | | | | | | Positive control |
|---|---|---|---|---|---|---|---|---|
| | 4 times | 8 times | 16 times | 32 times | 64 times | 128 times | 256 times | |
| 1 | 100 | 100 | 100 | — | — | — | — | 4.2 × $10^4$ |
| 5 | 100 | 100 | 100 | 94.83 | — | — | — | |
| 10 | 100 | 100 | 100 | 99.64 | — | — | — | |

4. Conclusion
The testing sample was reacted with *Eschetichia coli* 8099 for 1 min, 5 min, 10 min. The minimum inhibiting concentrations of the DDAPC are 0.006% (formulation 4), 0.003% (formulation 3), 0.003% (formulation 3) respectively.

Example 12

Effects of the Antimicrobial Composition Against *Bacillus subtilis* (Endo Spores)

1. Material
1) Testing strain: Variant of *Bacillus subtilis* (ATCC 9372), the 5th generations were used for testing; provided by the "Reserve Center of Chinese Microbial Reservation
2) Neutralizing agents: PBS solution containing 1% lecithin, 0.5%, NaSO3, 3% Tween-80. Concentration of bacteria used: 5×$10^5$~5×$10^6$ cuf/ml.
3) Testing sample: Formulation 2.
4) Interference organic matter: 3% Albumin Bovine (BSA) (filtered through 0.45 micron film to remove bacteria).
5) Concentration of the bacteria 1×$10^7$ cuf/ml~5×$10^7$ cuf/ml
2. Testing Methods and Procedures
Methods: GB15979-2002 <<Technical Standard for Testing Disinfection Product>>, item 2.1.1.2; 2.1.1.3; 2.2.5 and 2.1.1.7 "Suspension quantitative bactericidal tests"
1) Add 0.5 ml bacterial suspension and 0.5 ml 3% Bovine serum albumin (Organic interference Matter) to testing tube and mix together.
2) Put the testing tube in 20° C.±1° C. water bath for 5 min, add 4.0 ml testing sample to the tube and mix immediately and record the time.

3) At 2 min., 5 min., 10 min., 20 min. intervals, transfer 0.5 ml of the mixture to separate tubes and add to 4.5 ml neutralizing agents, mix well.
4) After 10 min. take 1.0 ml mixed liquid from each tube and count the survival bacteria number, inoculate 2 plates with liquid from each tube.
5) Use dilution liquid as positive control and perform parallel tests.
6) All the testing sample were incubated in 37 C incubator, observe the final results after 48 h.
7) The test was repeated one more time. The concentration of the viable bacteria count (cfu/ml) and their log value (N) was calculated.
Kill right value (KL)=the log value of average concentration of viable cell (No) of control group–the log value of average concentration of viable cell (Nx) of testing group.
The 80% diluted testing sample was used for Bactericidal tests, reacted with *Bacillus subtalis* for 2 min, 5 min, 10 min, 20 min respectively. Repeated the test two times at 20±1° C.
3. Results
At 20±1° C. condition the results of one repeat test showed that: 80% diluted sample reacted with *Bacillus subtalis* ATCC9372 for 2 min, the average Kill right value (KL)>5

2) Neutralizing agent: PBS solution containing 1% lecithin, 0.5%, NaSO3, 3% tween-80. Concentration of bacteria used: $5 \times 10^5 \sim 5 \times 10^6$ cuf/ml.
3) Testing sample: Formulation 1.
4) Organic Matter: 3% Albumin Bovine (BSA) (filtered through 0.45 micron film to remove bacteria).
2. Testing Methods and Procedures
Methods: "Procedures for testing bactericide affect" GB15979-2002 <<Technical Standard for Testing Disinfection Product>>, item 2.1.1.5; 2.1.1.7 and 2.1.1.9 "Suspension quantitative bactericidal tests"
Procedure of Suspension Quantitative Bactericidal Test
1) Add 0.5 ml bacterial suspension and 0.5 ml 3% Bovine serum albumin (Organic interference Matter) to testing tube and mix together.
2) Put the testing tube in 20° C.±1° C. water bath for 5 min, add 4.0 ml testing sample to the tube and mix immediately. Record the time.
3) At 2 min., 5 min., 10 min., 20 min. intervals, transfer 0.5 ml of the mixture to separate tubes and add to 4.5 ml neutralizing agent, mix well.
4) After 10 min. take 1.0 ml mixed liquid from each tube and count the survival bacteria number, inoculate 2 plates with liquid from each tube.

TABLE 9

The Effect of Antimicrobial Composition to *Bacillus subtilis*

| Testing Strain | Conc. of sample | KL of control | KL of different react time(min.) | | | |
|---|---|---|---|---|---|---|
| | | | 2 | 5 | 10 | 20 |
| *Bacillus subtalis* ATCC9372 | 80% diluted testing sample | 7.09 7.07-7.10 | >5 7.07-7.10 | >5 7.07-7.10 | >5 7.07-7.10 | >5 7.07-7.10 |

4. Conclusion
Under the organic matter interferences the tested material reacted with *Bacillus subtilis* for 2 min. the average kill right value (KL) were more than 5.

Example 13

Organic Matter Interference Tests

This test is to evaluate the antimicrobial effects of the antimicrobial composition under the influence of organic matters.
1. Materials
1) Testing strain: *Candida albicans* ATCC 10231, the 6th generations were used for testing; provided by the "Reserve Center of Chinese Microbial Reservation.

5) Use dilution liquid as positive control and perform parallel tests.
All the testing samples were incubated in 37 C incubator. Observe the final results after 48 h.
Kill right value(KL)=the log value of average concentration of viable cell (No) of control group–the log value of average concentration of viable cell (Nx) of testing group.
The 80% diluted testing sample was used for Bactericidal tests, reacted with *Candida albicans* for 2 min, 5 min, 10 min, 20 min respectively. Repeated the test three times at 20±1° C.
3. Results
At 20±1° C. condition the results of three tests showed that: 80% diluted sample reacted with *Candida albicans Candida albicans* ATCC 10231 for 2 min, the average Kill right value (KL)>4:

TABLE 10

The Influence of Organic Matter to Antimicrobial Composition

| Testing Strain | Conc. of sample | KL of control | KL of different react time(min.) | | | |
|---|---|---|---|---|---|---|
| | | | 2 | 5 | 10 | 20 |
| *Candida albicans* ATCC 10231 | 80% diluted testing sample | 6.34 6.34-6.34 | >4 5.34-6.34 | >4 6.34-6.34 | >4 6.34-6.34 | >4 6.34-6.34 |

4. Conclusion

Under the organic matter interferences the testing sample (80% dilution of Formulation 1) reacted with *Candida albicans* for 2 min. The average Kill right value(KL) were more than 4. The efficacy of the antimicrobial composition was not interfered by the organic matter. Stability of the Antimicrobial Compositions

Example 14

The antimicrobial efficacy of the antimicrobial composition after stored at raised temperature.

This test is to evaluate the antimicrobial effects of the aged antimicrobial composition, which is stored in 37 degree C. oven for three month.

1. Materials
1) Testing strain: *Candida albicans Candida albicans* ATCC 10231, the 5th generation incubations were used for testing. The strain was provided by the "Reserve Center of Chinese Microbial Reservation Committee".
2) Neutralizing agent: PBS solution containing 1% lecithin, 0.5%, NaSO3, 3% tween-80.
3) Testing sample: Formulation 1. The sample was heated at 37° C. for 90 days before the testing to evaluate accelerated stability, which equals 2 years at room temperature.

2. Testing Methods and Standards: <<Technical Standard for Disinfection>> (2002 Edition) "Procedures for testing bactericide effect" GB15979-2002 <<Technical Standard for Testing Disinfection Product>>

3. Results

The fungicide effect of testing sample to *Candida albicans* ATCC10231 showed: the undiluted and aged testing material reacted with *Candida albicans* ATCC 10231 for 2 min. the average fungicide rates were 99.98; reacted for 5, 10, 20 minutes, the average bactericide rates were 100%. (Table 11). The test repeated for two times.

TABLE 11

The Fungicidal Effect of aged Antimicrobial Composition

| Test | Fungicidal rates (%) of reaction time (min) | | | | Positive control (CFU/ml) |
|---|---|---|---|---|---|
| | 2 min | 5 min. | 10 min. | 20 min. | |
| 1 | 100 | 100.00 | 100.00 | 100.00 | $4.40 \times 10^4$ |
| 2 | 99.96 | 100.00 | 100.00 | 100.00 | $4.70 \times 10^4$ |

4. Conclusion

Testing sample heated at 37° C. for 90 days and then reacted with *Candida albicans* ATCC 10231, the average bactericide rate after 2 min. was 100%. The heat treated disinfectant showed the same fungicidal effect to *Candida albicans* as fresh prepared disinfectant solution.

Example 15

Stability Test of Freeze and Thaw

Place 20 ml of each of formulation 1, 2, 3, 4, 5, 6 in individual vials. The vials were frozen overnight and then were completely thawed at ambient temperature. The freeze/thaw cycles were repeated for 5 times. Results are illustrated in table 12.

TABLE 12

Results of Freeze and Thaw test of Antimicrobial Composition

| cycle | sample 1 | 2 | 3 | 4 | 5 | 6 |
|---|---|---|---|---|---|---|
| 1 | no separation no precipitation | no separation no precipitation | no separation no precipitation | no separation no precipitation | no separation no precipitation | no separation no precipitation |
| 2 | no separation no precipitation | no separation no precipitation | no separation no precipitation | no separation no precipitation | no separation no precipitation | no separation no precipitation |
| 3 | no separation no precipitation | no separation no precipitation | no separation no precipitation | no separation, no precipitation | no separation no precipitation | no separation no precipitation |
| 4 | no separation no precipitation | no separation no precipitation | no separation no precipitation | no separation no precipitation | no separation no precipitation | no separation no precipitation |
| 5 | no separation no precipitation | no separation no precipitation | no separation no precipitation | no separation no precipitation | no separation no precipitation | no separation no precipitation |

All the samples went through five cycles of the freeze and thaw test, no separation nor precipitation occurred in any of the tested solutions. The formulations 1, 2, 3, 4, 5, and 6 were not affected by the freeze/thaw treatments.

What is claimed is:

1. A method for disinfecting body surface, said method comprising administrating to body surface with a biocidal effective amount of a composition comprising:
   (a) a quaternary ammonium amino acid carboxylate salt selected from the group consisting of quaternary ammonium oxopyrrolidine-2-carboxylate, having the formula

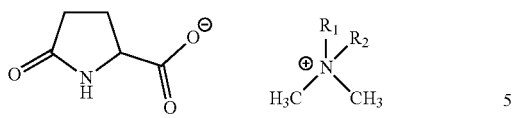

and quaternary ammonium N-acetylated alanine carboxylate, having the formula

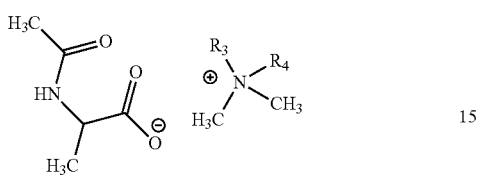

wherein R1, R2, R3, R4 independently are a C8-C14 alkyl group; and (b) a solvent selected from the group consisting of water, propylene glycol, polyethylene glycol, ethanol and a combination thereof.

2. The method of claim 1, wherein R1, R2, R3, R4 are the same C8-C14 alkyl group.

3. The method of claim 1, wherein R1, R2, R3, R4 are C10 alkyl, groups.

4. The method of claim 1, wherein R1, R2 are the same and R3, R4 are the same.

5. The method of claim 1, wherein the solvent is water.

* * * * *